United States Patent [19]

Muchowski et al.

[11] Patent Number: 4,988,822
[45] Date of Patent: Jan. 29, 1991

[54] INTERMEDIATES FOR PREPARING 5-AROYL-1,2-DIHYDRO-3H-PYRROLO(1,2-A)PYRROLE-1,1-DICARBOXYLATES

[75] Inventors: Joseph M. Muchowski, Sunnyvale; Robert Greenhouse, Cupertino, both of Calif.

[73] Assignee: Syntex (U.S.A.) Inc., Palo Alto, Calif.

[21] Appl. No.: 386,832

[22] Filed: Jul. 27, 1989

Related U.S. Application Data

[62] Division of Ser. No. 868,835, May 29, 1986, Pat. No. 4,873,340.

[51] Int. Cl.$^5$ .................. C07D 495/04; C07D 277/58; C07D 403/06
[52] U.S. Cl. ..................................... 548/539; 548/453; 548/336; 548/146; 548/121; 548/152
[58] Field of Search ............... 548/539, 453, 336, 146, 548/121, 152

[56] References Cited

U.S. PATENT DOCUMENTS

| | | | |
|---|---|---|---|
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,347,185 | 8/1982 | Muchowski et al. | 260/326.25 |
| 4,347,186 | 8/1982 | Muchowski et al. | 548/516 |
| 4,353,829 | 10/1982 | Thurber et al. | 260/326.25 |
| 4,456,759 | 6/1984 | Muchowski et al. | 548/453 X |
| 4,458,081 | 7/1984 | Muchowski et al. | 548/453 |
| 4,496,741 | 1/1985 | Doherty | 548/453 |
| 4,511,724 | 4/1985 | Chang et al. | 548/452 |
| 4,533,671 | 8/1985 | Biftu et al. | 514/413 |
| 4,536,512 | 8/1985 | Biftu et al. | 514/413 |

FOREIGN PATENT DOCUMENTS

| | | |
|---|---|---|
| 1151188 | 8/1983 | Canada . |
| 57-002269 | 1/1982 | Japan . |
| 2098989 | 12/1982 | United Kingdom . |

OTHER PUBLICATIONS

H. M. Gilow et al., J. Org. Chem., 1981, 46, 2221–2225.
R. K. Singh et al., J. Org. Chem., 1975, 40, 2969–2970.
D. M. Bailey et al., J. Med. Chem., 1973, 16, 1298–1300.
J. M. Muchowski et al., J. Med. Chem., 185, 28, 1037–1049.

*Primary Examiner*—David B. Springer
*Attorney, Agent, or Firm*—Derek P. Freyberg

[57] ABSTRACT

5-Aroyl-1,2-dihydro-3H-pyrrolo[1,2-a]pyrrole-1,1-dicarboxylates of the formula

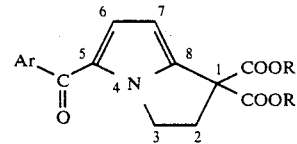

are prepared from 2-halopyrroles. Hydrolysis and β-decarboxylation of these compounds affords ketorolac and related compounds.

3 Claims, No Drawings

INTERMEDIATES FOR PREPARING 5-AROYL-1,2-DIHYDRO-3H-PYRROLO(1,2-A)PYRROLE-1,1-DICARBOXYLATES

CROSS-REFERENCE TO RELATED APPLICATION

This application is a divisional of our copending U.S. patent application Ser. No. 06/868,835, filed May 29, 1986, now U.S. Pat. No. 4,873,340.

BACKGROUND OF THE INVENTION

1. Field of the Invention

This invention relates to a process for preparing 5-aroyl-1,2-dihydro-3H-pyrrolo[1,2-a]pyrrole-1,1-dicarboxylates of formula I

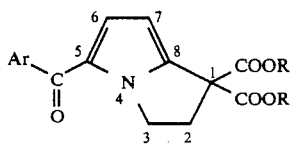

from 2-halopyrroles. Hydrolysis and β-decarboxylation of the compounds of formula I affords ketorolac and related compounds.

2. Background of the Invention

5-Aroyl-1,2-dihydro-3H-pyrrolo[1,2-a]pyrrole-1-carboxylic acids of formula II, and the pharmaceutically acceptable salts and esters thereof, are now under study as analgesic, anti-inflammatory, and anti-pyretic agents for mammals, including man. They are also smooth muscle relaxants. Two exemplary compounds under clinical study in man are ketorolac, 5-benzoyl-1,2-dihydro-3H-pyrrolo-[1,2-a]pyrrole-1-carboxylic acid, (II, Ar=C₆H₅), and anirolac, 5-p-anisoyl-1,2-dihydro-3H-pyrrolo[1,2-a]-pyrrole-1-carboxylic acid, (II, Ar=p—CH₃O—C₆H₅), both disclosed in U.S. Pat. No. 4,089,969 (Muchowski et al., assigned to Syntex (U.S.A.) Inc.). Other compounds, where the 5-aroyl substituents are substituted or unsubstituted benzoyl, furoyl, thenoyl, and pyrroyl, and where the 6- and/or 7-position on the pyrrolo-pyrrole nucleus is optionally substituted by lower alkyl or halogen, and uses thereof, are also disclosed in a series of patents assigned to Syntex (U.S.A.) Inc., beginning with U.S. Pat. No. 4,089,969, including U.S. Pat. Nos. 4,087,539; 4,097,579; 4,140,698; 4,232,038; 4,344,943; 4,347,186; 4,458,081; 4,347,187; 4,454,326; 4,347,185; 4,505,927; 4,456,759; 4,353,829; 4,397,862; 4,457,941; and 4,454,151. U.S. Pat. Nos. 4,511,724 and 4,536,512, assigned to Merck & Co., Inc., disclose 5-(substituted pyrrol-2-oyl)-1,2-dihydro-3H-pyrrolo-[1,2-a]pyrrole-1-carboxylic acid derivatives and 5-(1,2-dihydro-3H-pyrrolo[1,2-a]pyrrol-2-oyl)-1,2-dihydro-3H-pyrrolo[1,2-a]pyrrole-1-carboxylic acid derivatives, respectively.

Various methods for the preparation of these pyrrolo-pyrroles are exemplified in the patent and chemical literature.

For example, U.S. Pat. Nos. 4,347,186; 4,458,081; 4,347,187; and 4,454,326 disclose the preparation of 5-aroyl-pyrrolo-pyrroles from pyrroles, and certain intermediates, by the following route:

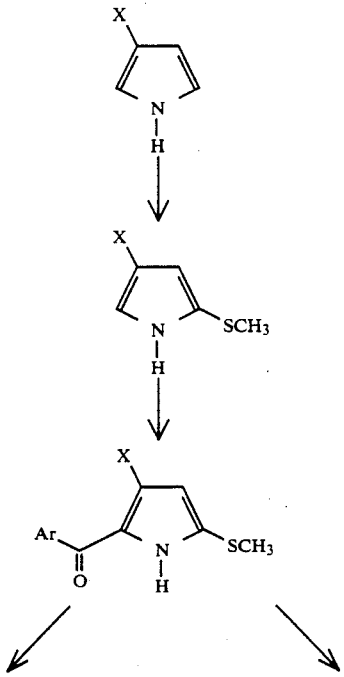

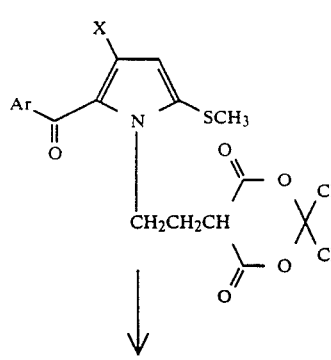
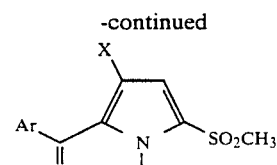
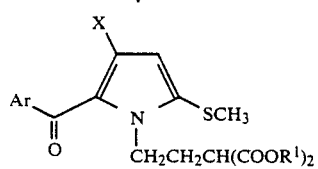
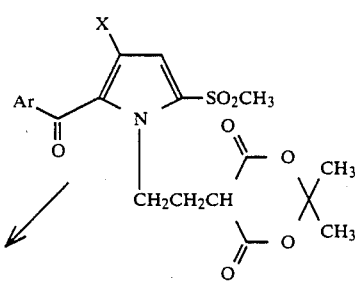
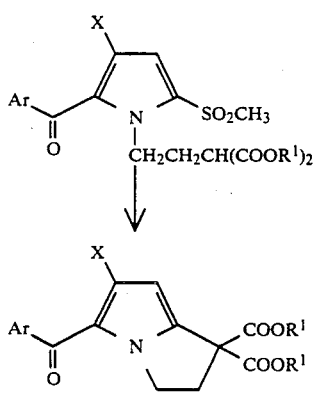

wherein:

$R^1$ and X are independently hydrogen or lower alkyl; and

Ar is a moiety selected from the group consisting of

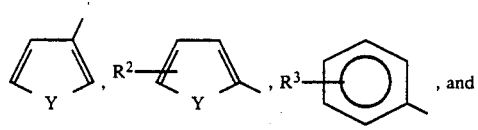 , and

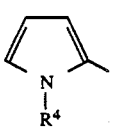

in which:

$R^2$ is hydrogen, methyl, chloro, or bromo, the $R^2$ substitution being at the 3-, 4- or 5-position of the ring;

$R^3$ is hydrogen, lower alkyl, lower alkoxycarboxyl, lower alkoxycarbonyl, lower alkylcarbonyl, fluoro, chloro or bromo, the $R^3$ substitution being at any available position in the ring;

$R^4$ is hydrogen or lower alkyl; and

Y is oxygen or sulfur.

Because this process introduces the leaving group (—$SO_2CH_3$) in a latent form (—$SCH_3$), an oxidation is required at some point in the process. Therefore, this process is not applicable to the synthesis of compounds containing functionalities, e.g. the —SR group, which are sensitive to the oxidation conditions. Thus, for example, 5-(4-methylthiobenzoyl)-1,2-dihydro-3H-pyrrolo-[1,2-a]pyrrole-1-carboxylic acid could not be prepared by this process.

U.S. Pat. Nos. 4,347,185; 4,505,927; and 4,456,759 disclose the preparation of 5-aroyl-pyrrolo-pyrroles from pyrroles, and certain intermediates, by the following route:

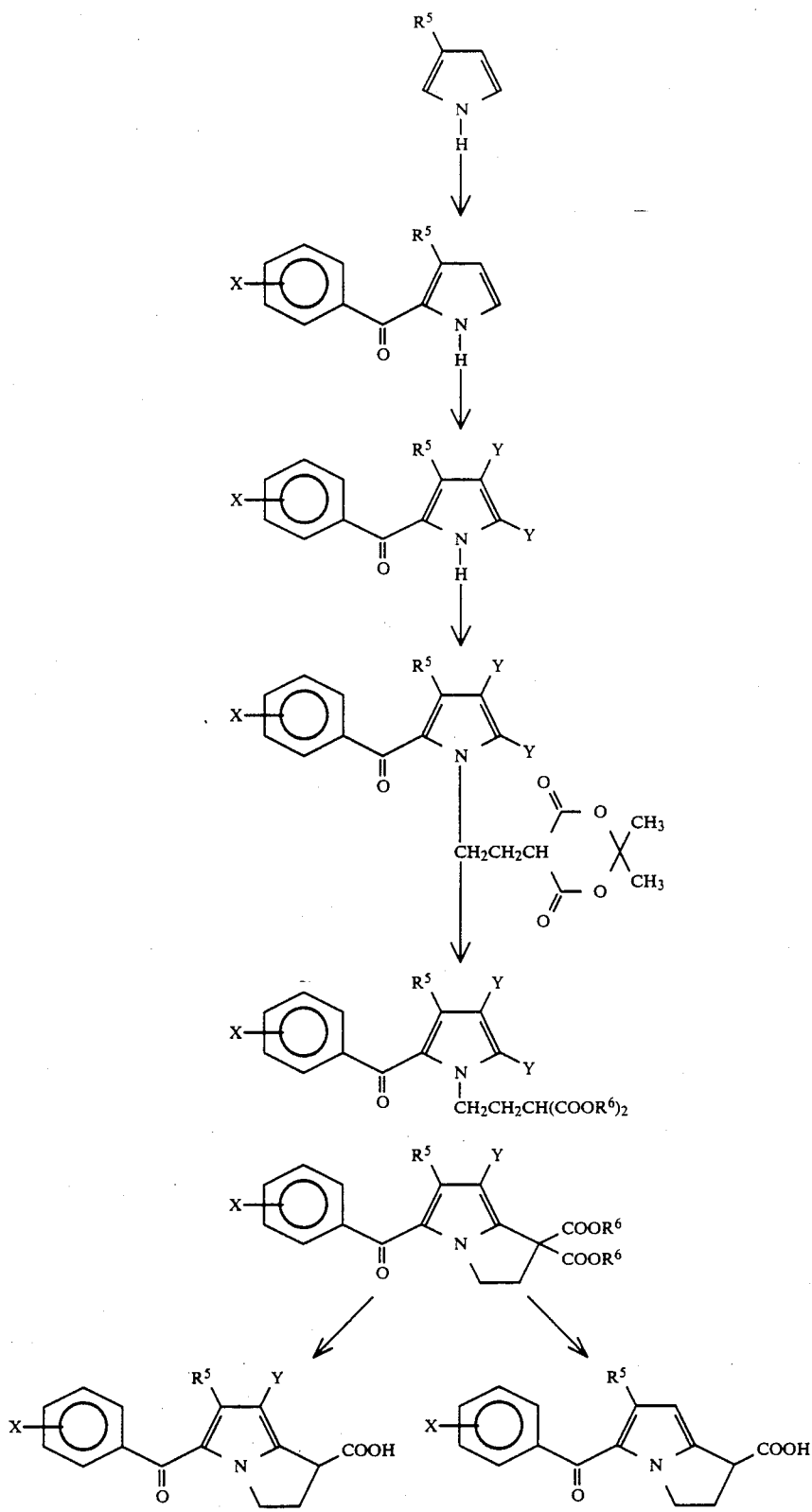
wherein:
R[5] is hydrogen or lower alkyl;
R[6] is lower alkyl;
X is hydrogen, lower alkyl, lower alkoxyl, lower alkoxycarbonyl, carboxyl, lower alkylcarbonyl, sulfonic acid, sulfonic acid alkyl ester, fluoro, chloro, or bromo; and
Y is chloro or bromo.
Because this process, when used to produce 7-unsubstituted-pyrrolo-pyrroles, requires removal of the 7- halogen by catalytic hydrogenation, it is not applicable to the synthesis of compounds containing functionalities, e.g. —Cl, —Br, —NO₂, —CH=CH₂, —CH≡CH, which are sensitive to the hydrogenation conditions. Thus, for example, neither 5-(4-chlorobenzoyl)-1,2-dihydro-3H-pyrrolo[1,2-a]pyrrole-1-carboxylic acid nor 5-(4-vinylbenzoyl)-1,2-dihydro-3H-pyrrolo[1,2-a]pyrrole-1-carboxylic acid could be prepared by this process.

SUMMARY OF THE INVENTION

In a first aspect, this invention relates to preparation of 5-aroyl-1,2-dihydro-3H-pyrrolo[1,2-a]pyrrole-1,1-dicarboxylates of Formula I

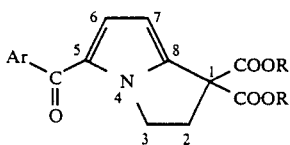

in which

R is lower alkyl; and

Ar is an aryl group not containing hydrogen bonded to a pyrrole nitrogen; from 2-halopyrroles.

The preparation may be represented schematically:

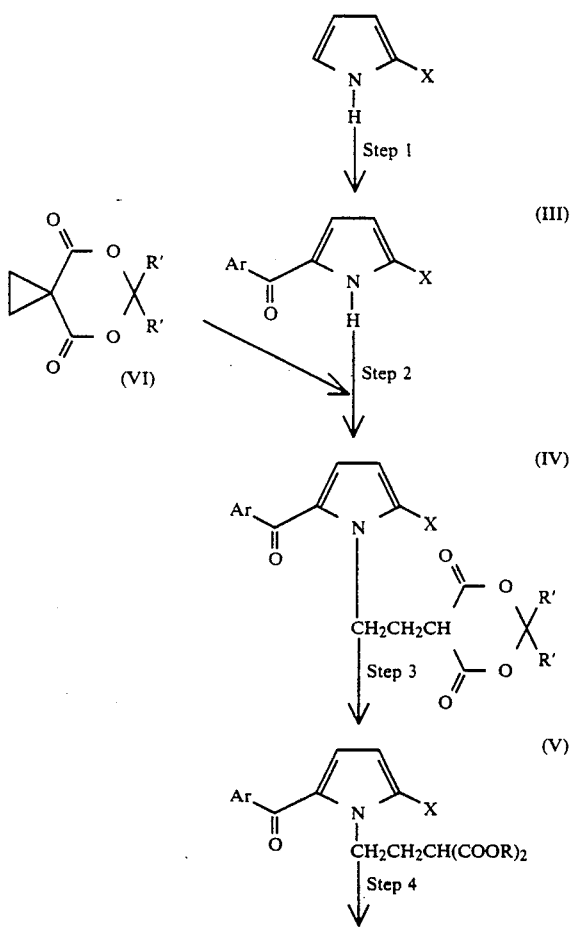

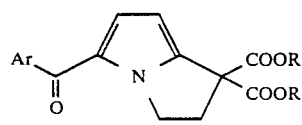

in which

R and Ar are as previously defined;

each R' is independently lower alkyl; and

X is bromo or chloro.

In a second aspect, this invention relates to the preparation of 5-aroyl-1,2-dihydro-3H-pyrrolo[1,2-a]-pyrrole-1-carboxylic acids by the preparation of compounds of formula I by the process described above, followed by decarboxylation thereof.

In a third aspect, this invention relates to novel compounds of formulae III, IV, and V, which are useful as intermediates in the process herein.

DETAILED DESCRIPTION OF THE INVENTION

Definitions

As used herein, "lower alkyl" means a branched or unbranched saturated hydrocarbon chain containing from one to six carbon atoms;

"lower alkenyl" means a branched or unbranched singly ethylenically unsaturated hydrocarbon chain containing from two to six carbon atoms;

"lower alkynyl" means a branched or unbranched singly acetylenically unsaturated hydrocarbon chain containing from two to six carbon atoms;

"strong mineral acid" means an inorganic, water-soluble, easily dissociable Bronsted-Lowry acid, such as hydrochloric, sulfuric, phosphoric acids, and the like;

"strong mineral base" means an inorganic, water-soluble base with a $pK_b$ less than about 5, such as sodium hydroxide, sodium carbonate, potassium bicarbonate, and the like; and "decarboxylation" of 1,1-dicarboxylates includes both hydrolysis and β-decarboxylation to leave the 1-carboxylic acid.

Preparation of Starting Materials

The starting 2-halopyrroles and compounds of formula VI, and the intermediates of formulae III, IV, and V may be isolated, if desired, using conventional techniques, including but not limited to filtration, distillation, crystallization, chromatography, and the like. Such intermediates may be characterized using conventional means, including physical constants and spectral characteristics.

The 2-halopyrroles, 2-chloropyrrole and 2-bromopyrrole, may be prepared by methods known to the art. See, for example, H. M. Gilow and D. E. Burton, J.Org.Chem., 46, 2221-5 (1981), which is incorporated herein by reference. As both of these pyrroles are relatively unstable, it is generally desirable that they be prepared relatively soon before use, that they be stabilized for storage with a base (such as a trialkylamine), and that they be refrigerated during storage, as set forth in the Gilow et al. article.

Compounds of formula VI, i.e. 6,6-di(lower alkyl)-5,7-dioxaspiro[2.5]octane-4,8-diones, may be prepared according to the method of Singh et al., J.Org.Chem., 40, 2969 (1975), which is incorporated herein by reference, for 6,6-dimethyl-5,7-dioxaspiro[2.5]octane-4,8- dione. Other spiro cyclopropyl compounds may be prepared in a manner similar to that for 6,6-dimethyl-5,7-dioxaspiro-[2.5]octane-4,8-dione, by substituting other ketones for acetone to form the dioxyketal ring. Thus, for example, 6,6-diethyl-5,7-dioxaspiro[2.5]octane-4,8-dione, 6-ethyl-6-methyl-5,7-dioxaspiro[2.5]octane-4,8-dione, and 6-methyl-6-propyl-5,7-dioxaspiro[2.5]octane-4,8-dione may be prepared using 3-pentanone, methyl ethyl ketone (2-butanone), and 2-pentanone, respectively. However, there is no particular advantage in varying the 6,6-substitution, since subsequent steps in the overall process remove these groups, and ease of removal is not enhanced by such variation, so that the 6,6-dimethyl compound is preferred.

Preparation of Compounds of Formula I

In Step 1, the process used is a Vilsmeier-Haack aroylation, i.e. the reaction of the 2-halopyrrole with the complex formed by the reaction of a compound of the formula ArC(O)Q, where Q is the residue (i.e. all but the N-bonded hydrogen atom) of a dialkylamine (e.g. dimethylamine, ethyl(methyl)amine, and the like) or a saturated cyclic amine (e.g. pyrrolidine, piperidine, morpholine, and the like) and an acid halide (e.g. phosphoryl chloride, phosphoryl bromide, thiophosphoryl chloride, thionyl chloride, thionyl bromide, phosgene, thiophosgene, oxalyl chloride, thiooxalyl chloride, and the like). Preferred compounds of the formula ArC(O)Q are the aryl morpholides, and a preferred acid halide is phosphoryl chloride. These reactions are described in U.S. Pat. Nos. 4,353,829 (morpholides); and 4,089,969 and 4,347,186 (diakylamides). If the acid halide and the halogen of the 2-halopyrrole differ, some "scrambling" of the halogen in the 5-aroyl-2-halopyrrole product will occur under the conditions of the Vilsmeier-Haack aroylation. For example, if 2-bromopyrrole is aroylated with benzmorpholide and phosphoryl chloride, the product will contain both 5-benzoyl-2-bromopyrrole and (predominantly) 5-benzoyl-2-chloropyrrole. This is not a particular problem, unless pure intermediates are desired, since the 2-halogen is lost in step 4 (the cyclization to form the pyrrolo[1,2-a]pyrrole nucleus). Additionally, aroyl halides may be used directly, obviating the need for phosphoryl chloride or other analogous acid halide. However, the resulting compounds of Formula III are new.

Preferred aryl groups not containing hydrogen bonded to a pyrrole nitrogen (Ar in formula I above) are those in which any pyrrole nitrogen present in the aryl group is substituted by lower alkyl, for example, those selected from the group consisting of

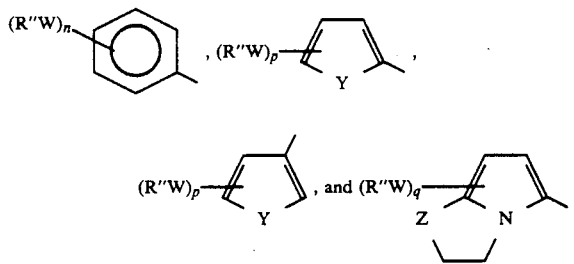

in which
R" is H, lower alkyl, lower alkenyl, or lower alkynyl, optionally substituted by halogen;
W is covalent bond, —O—, —S—, —S(O)—, —S(O)$_2$—, —NR—, —CHR—, —NO$_2$, fluoro, chloro, or bromo; except that if W is —NO$_2$, fluoro, chloro, or bromo, then R" is absent;
Y is —O—, —S—, or —NR—, with R being as defined above;
Z is —O—, —S—, —S(O)—, —S(O)—, —NR"—, or —CHR"—;
n is 0 to 5;
p is 0 to 3; and
q is 0 to 2;

The aryl dialkylamides, aryl morpholides, aroyl halides, etc. are readily preparable by methods set forth in U.S. Pat. Nos. 4,353,829; 4,089,969; 4,347,186; 4,511,724; 4,533,671; and 4,536,512, all of which are incorporated herein by reference.

A particularly preferred Ar is selected from 4-(R"W)-phenyls, especially phenyl, 4-methoxyphenyl, 4-methylthiophenyl, and 4-vinylphenyl.

In Step 2, the 5-aroyl-2-halopyrrole is treated with an excess, preferably a slight excess, of an alkali metal hydride or other strong base, preferably sodium hydride, under an inert atmosphere, e.g. nitrogen, neon and argon, preferably argon, until reaction is complete. This time may range from 10 minutes to 10 hours, but is ordinarily in the range of 1-2 hours. The reaction is slowed by cooling and takes place at about 0°-40° C., but preferably at room temperature i.e. 15°-25° C. Operable solvents include any polar aprotic organic solvent, e.g., dimethoxyethane (DME), bis(2-methoxyethyl) ether (diglyme), dimethylformamide (DMF), N-methylpyrrolidone (NMP), and the like; preferably DMF.

After the treatment with the hydride, a compound of formula VI is added in slight excess and the temperature is raised to about 50°-100° C., preferably 70°-80° C., and the mixture is allowed to react for about 1-10 hours or to completion. The product, a compound of formula IV, may be isolated, preferably as the salt.

In Step 3, the cyclic diester dissolved in a suitable solvent, e.g. an alcohol, is converted to the corresponding dialkyl dicarboxylate by treatment with a suitable alcohol in the presence of acid. In a preferred embodiment the compound of formula IV is dissolved in methanol previously saturated with HCl at about 0°-30° C., preferably 0°-20° C., for about 5 minutes to 5 hours, preferably 30 minutes to 3 hours. The dimethyl or other dialkyl ester may then be recovered by suitable conventional techniques, to afford compounds of formula V, the 1-(2-ethylmalonate) derivative of the 5-aroyl-2-halopyrrole.

Cyclization to the corresponding pyrrolo[1,2-a]-pyrrole compound of Formula I takes place in Step 4. Here, the compound of formula V is dissolved in a polar aprotic organic solvent, preferably DMF, and treated with a slight excess of an alkali metal hydride, preferably sodium hydride in mineral oil. The reaction mixture may be heated to about 50°-150° C. for about 10 minutes to 10 hours, preferably to 100°-110° C. for 4-6 hours. All of these operations are carried out in an inert atmosphere, preferably under nitrogen or argon. The mixture is then cooled to about 5°-40° C. preferably room temperature (15°-25° C.) and the solution made acidic by addition of a dilute strong mineral acid, preferably by addition of 10% hydrochloric acid. The product of Formula I may then be recovered.

Preparation of Compounds of Formula II

The compounds of Formula I may then be converted to the corresponding 5-aroyl-1,2-dihydro-3H-pyrrolo[1,2-a]-pyrrole-1-carboxylic acids by the methods described in U.S. Pat. No. 4,347,186, which consist of treatment with base to accelerate ester hydrolysis, followed by treatment with acid to effect decarboxylation.

Novel Intermediates

The compounds of formula III, IV, and V are novel, and are useful as intermediates in preparing compounds of formula II, which are therapeutically useful as discussed hereinbefore.

EXAMPLES

The following examples illustrate the present invention, and should not be construed to limit it.

EXAMPLE 1

Preparation of 2-chloropyrrole

A. Pyrrole was chlorinated according to the procedure of H. M. Gilow and D. E. Burton, J.Org.Chem., 46, 2221-5 (1981), to provide 2-chloropyrrole. Thus, pyrrole (0.70 mL, 0.67 g, 10 mmol) was dissolved in anhydrous THF (50 mL, freshly distilled from lithium aluminum hydride), and the solution was cooled to −78° C. in a dry-ice/isopropanol bath. N-chlorosuccinimide (1.33 g, 10 mmol) was added in a single portion, and the solution stirred at this temperature for one hour. The solution was kept in a freezer under nitrogen at −12° C. overnight, during which time the N-chlorosuccinimide dissolved totally and the solution became darker in color. After a total of 20 hours at this temperature, three drops of pyridine were added to the mixture, and the solution containing the crude product was chromatographed on alumina (Fluka, 3% water added, 30×4 cm column), eluting the product with ethyl acetate/hexane (1:19). The product in solution was received into a flask containing 1 mL triethylamine and anhydrous sodium sulfate. The solution was filtered from the drying agent and evaporated to dryness at reduced pressure. The 2-chloropyrrole thus obtained was used without further purification.

B. Substituting N-bromosuccinimide for N-chlorosuccinimide, and using a similar procedure to that in part A of this Example, one obtains 2-bromopyrrole.

EXAMPLE 2

Preparation of 5-(4-chlorobenzoyl)-2-chloropyrrole (Step 1)

A. Under strictly anhydrous conditions, 4-chlorobenzmorpholide (1.79 g, 8 mmol) was mixed with phosphoryl chloride (3.066 g, 1.87 mL, 20 mmol) in a 500 mL round-bottom flask fitted with a calcium chloride drying tube. The mixture was stirred for 18 hours at 25°-30° C. (oil bath, external temperature). The 2-chloropyrrole from Example 1A was dissolved in 1,2-dichloroethane (250 mL) and added dropwise to the Vilsmeier complex. Stirring at 25°-30° C. was continued for an additional 15 hours, at which time the mixture was cooled to 0° C. and aqueous sodium carbonate (10%, 100 mL) was cautiously added. The mixture was heated to reflux for 30 minutes, cooled, and extracted with dichloromethane (3×250 mL), dried over sodium sulfate, and evaporated to dryness. The crude product thus obtained was chromatographed on silica gel (100 g, hexane/ethyl acetate, 9:1), and afforded 1.35 g (71%) of a colorless crystalline product, which was crystallized from hexane/ethyl acetate to give 5-(4-chlorobenzoyl)-2-chloropyrrole, having the following properties:

m.p. 210°-211° C.;
UV: (MeOH) 211, 252, 312 nm ($\epsilon$12,000, 11,200; 19,100); M.S. 243, 241, 239 (M+);
For $C_{11}H_7Cl_2NO$: Calc. C, 55.02; H, 2.94; N, 5.83; Found: C, 55.08, H, 3:06; N, 5.77.

B. Substituting for 4-chlorobenzomorpholide, in the procedure of Part A of this Example,
benzmorpholide,
4-methoxybenzmorpholide,
4-methylthiobenzmorpholide,
4-vinylbenzmorpholide,
2,4-dichlorobenzmorpholide,
3-methylbenzmorpholide,
2-furoylmorpholide,
2-theonylmorpholide,
3-thenoylmorpholide,
3-ethyl-2-thenoylmorpholide,
4-n-butyl-2-furoylmorpholide, or
1-methyl-2-pyrroylmorpholide,
one obtains, respectively,
5-benzoyl-2-chloropyrrole,
5-(4-methoxybenzoyl)-2-chloropyrrole,
5-(4-methylthiobenzoyl)-2-chloropyrrole,
5-(4-vinylbenzoyl)-2-chloropyrrole,
5-(2,4-dichlorobenzoyl)-2-chloropyrrole,
5-(3-methylbenzoyl)-2-chloropyrrole,
5-(2-furoyl)-2-chloropyrrole,
5-(2-thenoyl)-2-chloropyrrole,
5-(3-thenoyl)-2-chloropyrrole,
5-(3-ethyl-2-thenoyl)-2-chloropyrrole,
5-(4-n-butyl-2-furoyl)-2-chloropyrrole, or
5-(1-methyl-2-pyrroyl)-2-chloropyrrole.

Similarly, substituting N,N-dialkylarylamides for the arylmorpholides, and using the procedures for U.S. Pat. No. 4,089,969 etc., one obtains 5-aroyl-2-chloropyrroles.

C. Substituting 2-bromopyrrole for 2-chloropyrrole and phosphoryl bromide for phosphoryl chloride, and using a similar procedure to that in Part A of this Example, one obtains 5-(4-chlorobenzoyl)-2-bromopyrrole.

Similarly, substituting other arylmorpholides for 4-chlorobenzmorpholides, one obtains 5-aroyl-2-bromopyrroles. Also, substituting N,N-dialkylarylamides for the arylmorpholides, and using the procedures of U.S. Pat. No. 4,089,969 etc., one obtains 5-aroyl-2-bromopyrroles.

EXAMPLE 3

Preparation of
5-(4-chlorobenzoyl)-2-chloro-1-[2-(2,2-dimethyl-4,6-dioxo-1,3-dioxan-5-yl)ethyl]pyrrole (Step 2)

A. 5-(4-chlorobenzoyl)-2-chloropyrrole (1,700 g, 7.08 mmol) was dissolved in DMF (10 ml), and the solution added slowly, under nitrogen, to a suspension of 60% sodium hydride in mineral oil (0.310 g, 7.78 mmol) in dry DMF (10 ml). The resulting mixture was stirred for one hour at room temperature, after which the 6,6-dimethyl-5,7-dioxa-spiro[2.5]octane-4,8-dione (1.324 g, 7.78 mmol) was added in one portion, and the reaction temperature was raised to 70°-80° C. (oil bath, external temperature) for six hours. Upon cooling the solution was poured into ether (600 ml, reagent grade) and stirred for one hour. The precipitated solid so obtained was filtered and washed with ether (100 ml), and dried under vacuum for one hour. The 5-(4-chlorobenzoyl)-2-chloro-1-[2-(2,2-dimethyl-4,6-dioxo-1,3-dioxan-5-yl)ethyl]pyrrole thus obtained (as the sodium salt) was used without further purification.

B. Substituting for 5-(4-chlorobenzoyl)-2-chloropyrrole, in the procedure of part A of this Example,
  5-benzoyl-2-chloropyrrole,
  5-(4-methoxybenzoyl)-2-chloropyrrole,
  5-(4-methylthiobenzoyl)-2-chloropyrrole,
  5-(4-vinylbenzoyl)-2-chloropyrrole,
  5-(2,4-dichlorobenzoyl)-2-chloropyrrole,
  5-(3-methylbenzoyl)-2-chloropyrrole,
  5-(2-furoyl)-2-chloropyrrole,
  5-(2-thenoyl)-2-chloropyrrole,
  5-(3-thenoyl)-2-chloropyrrole,
  5-(3-ethyl-2-thenoyl)-2-chloropyrrole,
  5-(4-n-butyl-2-furoyl)-2-chloropyrrole, or
  5-(1-methyl-2-pyrroyl)-2-chloropyrrole,
one obtains, respectively,
  5-benzoyl-2-chloro-1-[2-(2,2-dimethyl-4,6-dioxo-1,3-dioxan-5-yl)ethyl]pyrrole,
  5-(4-methoxybenzoyl)-2-chloro-1-[2-(2,2-dimethyl-4,6-dioxo-1,3-dioxan-5-yl)ethyl]pyrrole,
  5-(4-methylthiobenzoyl)-2-chloro-1-[2-(2,2-dimethyl-4,6-dioxo-1,3-dioxan-5-yl)ethyl]pyrrole,
  5-(4-vinylbenzoyl)-2-chloro-1-[2-(2,2-dimethyl-4,6-dioxo-1,3-dioxan-5-yl)ethyl]pyrrole,
  5-(2,4-dichlorobenzoyl)-2-chloro-1-[2-(2,2-dimethyl-4,6-dioxo-1,3-dioxan-5-yl)ethyl]pyrrole,
  5-(3-methylbenzoyl)-2-chloro-1-[2-(2,2-dimethyl-4,6-dioxo-1,3-dioxan-5-yl)ethyl]pyrrole,
  5-(2-furoyl)-2-chloro-1-[2-(2,2-dimethyl-4,6-dioxo-1,3-dioxan-5-yl)ethyl]pyrrole,
  5-(2-thenoyl)-2-chloro-1-[2-(2,2-dimethyl-4,6-dioxo-1,3-dioxan-5-yl)ethyl]pyrrole,
  5-(3-thenoyl)-2-chloro-1-[2-(2,2-dimethyl-4,6-dioxo-1,3-dioxan-5-yl)ethyl]pyrrole,
  5-(3-ethyl-2-thenoyl)-2-chloro-1-[2-(2,2-dimethyl-4,6-dioxo-1,3-dioxan-5-yl)ethyl]pyrrole,
  5-(4-n-butyl-2-furoyl)-2-chloro-1-[2-(2,2-dimethyl-4,6-dioxo-1,3-dioxan-5-yl)ethyl]pyrrole, or
  5-(1-methyl-2-pyrroyl)-2-chloro-1-[2-(2,2-dimethyl-4,6-dioxo-1,3-dioxan-5-yl)ethyl]pyrrole.

C. Substituting 5-(4-chlorobenzoyl)-2-bromopyrrole for 5-(4-chlorobenzoyl)-2-chloropyrrole in the procedure of part A of this Example, one obtains 5-(4-chlorobenzoyl)-2-bromo-1-[2-(2,2-dimethyl-4,6-dioxo-1,3-dioxo-1,3-dioxan-5-yl)ethyl]pyrrole.

Similarly, substituting other 5-aroyl-2-bromopyrroles, one obtains other 5-aroyl-2-bromo-1-[2-(2,2-dimethyl-4,6-dioxo-1,3-dioxan-5-yl)ethyl]pyrroles.

EXAMPLE 4

Preparation of 5-(4-chlorobenzoyl)-2-chloro-1-[3,3-di(methoxycarbonyl)propyl]pyrrole (Step 3)

A. The 5-(4-chlorobenzoyl)-2-chloro-1-[2-(2,2-dimethyl-4,6-dioxo-1,3-dioxan-5-yl)ethyl]pyrrole sodium salt from Example 3A was dissolved in methanol saturated with hydrogen chloride (30 ml) and stirred at 0° C. for three hours. The solution was diluted with methanol (30 ml) and allowed to warm to room temperature, and was then stirred for another four hours. The solvent was then evaporated under reduced pressure at 10°–20° C. The residue was partitioned between ether and water (150 ml+150 ml), and the water was extracted with ether (2×150 ml). The combined ether extracts were dried over anhydrous sodium sulfate and evaporated to dryness. The residue was chromatographed on Florisil® (50 g/g mixture), eluting the product with hexane/ethyl acetate, 7:3. The product so obtained (1.912 g, 68%) was a colorless crystalline solid, which was recrystallized from dichloromethane/hexane to afford 5-(4-chlorobenzoyl)-2-chloro-1-[3,3-di(methoxycarbonyl)propyl]pyrrole, having the following properties:

m.p. 72.5°–73.5° C. (corr.);
UV: (MeOH 209, 254, 308 nm (ε 11,200; 10,700; 17,000); M.S. 399, 397 (M+);
For $C_{18}H_{17}Cl_2NO_5$: Calc.: C, 54.28; H, 4.30; N, 3.51; Found: C, 54.07; H, 4.32; N, 3.50.

B. Substituting for 5-(4-chlorobenzoyl)-2-chloro-1-[2-(2,2-dimethyl-4,6-dioxo-1,3-dioxan-5-yl)ethyl]-pyrrole, in the procedure of part A of this Example,
  5-benzoyl-2-chloro-1-[2-(2,2-dimethyl-4,6-dioxo-1,3-dioxan-5-yl)ethyl]pyrrole,
  5-(4-methoxybenzoyl)-2-chloro-1-[2-(2,2-dimethyl-4,6-dioxo-1,3-dioxan-5-yl)ethyl]pyrrole,
  5-(4-methylthiobenzoyl)-2-chloro-1-[2-(2,2-dimethyl-4,6-dioxo-1,3-dioxan-5-yl)ethyl]pyrrole,
  5-(4-vinylbenzoyl)-2-chloro-1-[2-(2,2-dimethyl-4,6-dioxo-1,3-dioxan-5-yl)ethyl]pyrrole,
  5-(2,4-dichlorobenzoyl)-2-chloro-1-[2-(2,2-dimethyl-4,6-dioxo-1,3-dioxan-5-yl)ethyl]pyrrole,
  5-(3-methylbenzoyl)-2-chloro-1-[2-(2,2-dimethyl-4,6-dioxo-1,3-dioxan-5-yl)ethyl]pyrrole,
  5-(2-furoyl)-2-chloro-1-[2-(2,2-dimethyl-4,6-dioxo-1,3-dioxan-5-yl)ethyl]pyrrole,
  5-(2-thenoyl)-2-chloro-1-[2-(2,2-dimethyl-4,6-dioxo-1,3-dioxan-5-yl)ethyl]pyrrole,
  5-(3-thenoyl)-2-chloro-1-[2-(2,2-dimethyl-4,6-dioxo-1,3-dioxan-5-yl)ethyl]pyrrole,
  5-(3-ethyl-2-thenoyl)-2-chloro-1-[2-(2,2-dimethyl-4,6-dioxo-1,3-dioxan-5-yl)ethyl]pyrrole,
  5-(4-n-butyl-2-furoyl)-2-chloro-1-[2-(2,2-dimethyl-4,6-dioxo-1,3-dioxan-5-yl)ethyl]pyrrole, or
  5-(1-methyl-2-pyrroyl)-2-chloro-1-[2-(2,2-dimethyl-4,6-dioxo-1,3-dioxan-5-yl)ethyl]pyrrole, one obtains respectively,
  5-benzoyl-2-chloro-1-[3,3-di(methoxycarbonyl)propyl]-pyrrole,
  5-(4-methoxybenzoyl)-2-chloro-1-[3,3-di(methoxycarbonyl)propyl]pyrrole,
  5-(4-methylthiobenzoyl)-2-chloro-1-[3,3-di(methoxycarbonyl)propyl]pyrrole,
  5-(4-vinylbenzoyl)-2-chloro-1-[3,3-di(methoxycarbonyl)propyl]pyrrole,
  5-(2,4-dichlorobenzoyl)-2-chloro-1-[3,3-di(methoxycarbonyl)propyl]pyrrole,
  5-(3-methylbenzoyl)-2-chloro-1-[3,3-di(methoxycarbonyl)propyl]pyrrole,
  5-(2-furoyl)-2-chloro-1-[3,3-di(methoxycarbonyl)propyl]pyrrole,
  5-(2-thenoyl)-2-chloro-1-[3,3-di(methoxycarbonyl)propyl]pyrrole,
  5-(3-thenoyl)-2-chloro-1-[3,3-di(methoxycarbonyl)propyl]pyrrole,
  5-(3-ethyl-2-thenoyl)-2-chloro-1-[3,3-di(methoxycarbonyl)propyl]pyrrole,
  5-(4-n-butyl-2-furoyl)-2-chloro-1-[3,3-di(methoxycarbonyl)propyl]pyrrole, or
  5-(1-methyl-2-pyrroyl)-2-chloro-1-[3,3-di(methoxycarbonyl)propyl]pyrrole.

C. Substituting 5-(4-chlorobenzoyl)-2-bromo-1-[2-(2,2-dimethyl-4,6-dioxo-1,3-dioxan-5-yl)ethyl]pyrrole for 5-(4-chlorobenzoyl)-2-chloro-1-[2-(2,2-dimethyl-4,6-dioxo-1,3-dioxan-5-yl)ethyl]pyrrole in the procedure of part A of this Example, one obtains 5-(4-chlorobenzoyl)-2-bromo-1-[3,3-di(methoxycarbonyl)propyl]pyrrole.

Similarly, substituting other 5-aroyl-2-bromo-1-[2-(2,2-dimethyl-4,6-dioxo-1,2-dioxan-5-yl)ethyl]pyrroles, one obtains other 5-aroyl-2-bromo-1-[3,3-di(methoxycarbonyl)propyl]pyrroles.

D. Substituting other lower alkyl alcohols for the methanol in the procedure of Parts A through C of this Example, one obtains other di(lower alkyl) malonate esters.

EXAMPLE 5

Preparation of dimethyl 5-(4-chlorobenzoyl)-1,2-dihydro-3H-pyrrolo[1,2-a]pyrrole-1,1-dicarboxylate (Step 4)

A. 5-(4-Chlorobenzoyl)-2-chloro-1-[3,3-di-(methoxycarbonyl)propyl]pyrrole (1.550 g, 3.89 mmol) was dissolved in anhydrous DMF (25 ml). Sodium hydride (60% in mineral oil, 0.171 g, 4.28 mmol) was added in a single portion under a nitrogen atmosphere, and the reaction mixture was heated with stirring to 100° C. (oil bath, internal temperature) for 4 hours. Upon cooling, the mixture was diluted with ether (300 ml) and washed with water (2×400 ml). The water wash was saturated with salt and extracted with benzene (2×50 ml). The combined organic phases were drived over sodium sulfate, evaporated to dryness, and dried under vacuum. The residue, dimethyl 5-(4-chlorobenzoyl)-1,2-dihydro-3H-pyrrolo[1,2-a]pyrrole-1,1-dicarboxylate, was carried to the next step without further purification.

B. Substituting for 5-(4-chlorobenzoyl)-2-chloro-1-[3,3-(dimethoxycarbonyl)propyl]pyrrole, in the procedure of part A of this Example, 5-benzoyl-2-chloro-1-[3,3-di(methoxycarbonyl)propyl]pyrrole,
5-(4-methoxybenzoyl)-2-chloro-1-[3,3-di(methoxycarbonyl)propyl]pyrrole,
5-(4-methylthiobenzoyl)-2-chloro-1-[3,3-di(methoxycarbonyl)propyl]pyrrole,
5-(4-vinylbenzoyl)-2-chloro-1-[3,3-di(methoxycarbonyl)propyl]pyrrole,
5-(2,4-dichlorobenzoyl)-2-chloro-1-[3,3-di(methoxycarbonyl)propyl]pyrrole,
5-(3-methylbenzoyl)-2-chloro-1-[3,3-di(methoxycarbonyl)propyl]pyrrole,
5-(2-furoyl)-2-chloro-1-[3,3-di(methoxycarbonyl)propyl]pyrrole,
5-(2-thenoyl)-2-chloro-1-[3,3-di(methoxycarbonyl)propyl]pyrrole,
5-(3-thenoyl)-2-chloro-1-[3,3-di(methoxycarbonyl)propyl]pyrrole,
5-(3-ethyl-2-thenoyl)-2-chloro-1-[3,3-di(methoxycarbonyl)propyl]pyrrole,
5-(4-n-butyl-2-furoyl)-2-chloro-1-[3,3-di(methoxycarbonyl)propyl]pyrrole, or
5-(1-methyl-2-pyrroly)-2-chloro-1-[3,3-di(methoxycarbonyl)propyl]pyrrole,
one obtains, respectively,
dimethyl 5-benzoyl-1,2-dihydro-3H-pyrrolo[1,2-a]pyrrole-1,1-dicarboxylate,
dimethyl 5-(4-methoxybenzoyl)-1,2-dihydro-3H-pyrrolo[1,2-a]pyrrole-1,1-dicarboxylate,
dimethyl 5-(4-methylthiobenzoyl)-1,2-dihydro-3H-pyrrolo[1,2-a]pyrrole-1,1-dicarboxylate,
dimethyl 5-(4-vinylbenzoyl)-1,2-dihydro-3H-pyrrolo[1,2-a]pyrrole-1,1-dicarboxylate,
dimethyl 5-(2,4-dichlorobenzoyl)-1,2-dihydro-3H pyrrolo[1,2-a]pyrrole-1,1-dicarboxylate,
dimethyl 5-(3-methylbenzoyl)-1,2-dihydro-3H pyrrolo[1,2-a]pyrrole-1,1-dicarboxylate,
dimethyl 5-(2-furoyl)-1,2-dihydro-3H-pyrrolo[1,2-a]-pyrrole-1,1-dicarboxylate,
dimethyl 5-(2-thenoyl)-1,2-dihydro-3H-pyrrolo[1,2-a]-pyrrole-1,1-dicarboxylate,
dimethyl 5-(3-thenoyl)-1,2-dihydro-3H-pyrrolo[1,2-a]-pyrrole-1,1-dicarboxylate,
dimethyl 5-(3-ethyl-2-thenoyl)-1,2-dihydro-3H-pyrrolo[1,2-a]pyrrole-1,1-dicarboxylate,
dimethyl 5-(4-n-butyl-2-furoyl)-1,2-dihydro-3H-pyrrolo[1,2-a]pyrrole-1,1-dicarboxylate, or
dimethyl 5-(1-methyl-2-pyrroyl)-1,2-dihydro-3H-pyrrolo[1,2-a]pyrrole-1,1-dicarboxylate, C. Substituting 5-(4-chlorobenzoyl)-2-bromo-1-[3,3-di(methoxycarbonyl)propyl]pyrrole for 5-(4-chlorobenzoyl)-2-chloro-1-[3,3-di(methoxycarbonyl)-propyl]pyrrole in the procedure of part A of this Example, one obtains dimethyl 5-(4-chlorobenzoyl)-1,2-dihydro-3H-pyrrolo-[1,2-a]pyrrole-1,1-dicarboxylate.

Similarly, substituting other 5-aroyl-2-bromo-1-[3,3-di(methoxycarbonyl)propyl]pyrroles for 5-(4-chlorobenzoyl)-2-bromo-1-[3,3-di(methoxycarbonyl)propyl]pyrrole, one obtains other dimethyl 5-aroyl-1,2-dihydro-3H-pyrrolo[1,2-a]pyrrole-1,1-dicarboxylates.

D. Substituting other di(lower alkyl) malonate esters for the dimethyl ester in the procedure of Parts A through C of this Example, one obtains other di(lower alkyl) pyrrolo[1,2-a]pyrrole-1,1-dicarboxylates.

EXAMPLE 6

Preparation of 5-(4-chlorobenzoyl)-1,2-dihydro-3H-pyrrolo[1,2-a]pyrrole-1-carboxylic acid The residue of dimethyl 5-(4-chlorobenzoyl)-1,2-dihydro-3H-pyrrolo[1,2-a]pyrrole-1,1-dicarboxylate from Example 5 (1.930 g) was dissolved in methanol (50 ml), and was treated with aqueous sodium hydroxide (10%, 10 ml). The mixture was heated to reflux under nitrogen for one hour. Upon cooling, the solvent was removed under reduced pressure. The solid residue was partitioned between ether and water (100 ml+100 ml), and acidified with 1:10 hydrochloric acid/water (20 ml, pH≈4). Some of the acid thus formed precipitated, so enough ethyl actate was added to dissolve the product, and the phases were separated. The water was extracted with ethyl acetate (2×100 ml), and the organic extracts were dried over sodium sulfate and evaporated to dryness. The crude product was recrystallized from ethyl acetate to give 0.525 g (47%) crystalline material, m.p. 198° C. (corr.). The mother liquor was purified by preparative thin layer chromatography on silica, eluting with chloroform/methanol/acetic acid (60:10:1), to give another 0.375 g (33%). The total yield of homogenous 5-(4-chlorobenzoyl)-1,2-dihydro-3H-pyrrolo[1,2-a]pyrrole-1-carboxylic acid was 0.900 g (80%), m.p. 198° C. (mixed m.p. with authentic sample prepared by another route: 199° C.). The IR and NMR spectral properties were identical to those of the authentic specimen.

Other 1-carboxylic acids may be prepared from 1,1-dicarboxylates by similar methods.

What is claimed is:

1. A compound of the formula

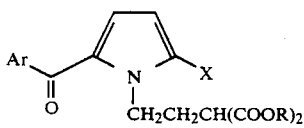

in which

R is lower alkyl;

X is bromo or chloro; and

Ar is selected from the group consisting of

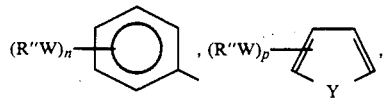

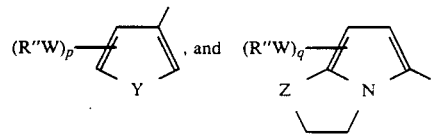

in which

R" is H, lower alkyl, lower alkenyl, or lower alkynyl, optionally substituted by halogen;

W is a covalent bond, —O—, —S—, —S(O)—, —S(O)$_2$—, —NR—, —CHR—, —NO$_2$, fluoro, chloro, or bromo; except that if W is —NO$_2$, fluoro, chloro, or bromo, then R" is absent;

Y is —O—, —S—, or —NR—;

Z is —O—, —S—, —S(O)—, —S(O)$_2$—, —NR"—, or —CHR"—;

n is 0 to 5;

p is 0 to 3; and q is 0 to 2.

2. The compound of claim 1 wherein R is methyl, X is chloro, and Ar is selected from 4-(R"W)-phenyls.

3. The compound of claim 2 wherein Ar is phenyl.

* * * * *